United States Patent
Urfer et al.

[11] Patent Number: 6,087,320
[45] Date of Patent: *Jul. 11, 2000

[54] VISCOSITY-ADJUSTED SURFACTANT CONCENTRATE COMPOSITIONS

[75] Inventors: Allen D. Urfer, Landsdale; Virginia Lazarowitz, Hatfield, both of Pa.; Patricia E. Bator, Secaucus; Barry A. Salka, Fair Lawn, both of N.J.; Robert A. Aleksejczyk, Hatfield, Pa.

[73] Assignee: Henkel Corp., Gulph Mills, Pa.

[ * ] Notice: This patent is subject to a terminal disclaimer.

[21] Appl. No.: 08/638,395

[22] Filed: Apr. 25, 1996

Related U.S. Application Data

[63] Continuation of application No. 08/313,652, Sep. 26, 1994, abandoned, which is a continuation of application No. 07/899,561, Jun. 16, 1992, abandoned, which is a continuation-in-part of application No. 07/644,470, Jan. 18, 1991, Pat. No. 5,242,615, which is a continuation of application No. 07/406,992, Sep. 14, 1989, abandoned.

[51] Int. Cl.⁷ ............... C11D 1/74; C11D 1/02; C11D 1/83
[52] U.S. Cl. ............ 510/470; 510/123; 510/126; 510/127; 510/158; 510/159; 510/403; 510/404; 510/427; 510/490; 510/497; 510/535; 510/536; 510/537
[58] Field of Search ............... 510/470, 403, 510/404, 427, 490, 497, 123–128, 159, 158, 535–537; 252/FOR 239

[56] References Cited

U.S. PATENT DOCUMENTS

| | | | |
|---|---|---|---|
| 3,920,563 | 11/1975 | Wixon | 252/8.75 |
| 3,954,679 | 5/1976 | Wixon | 252/555 |
| 3,985,687 | 10/1976 | Inamorato et al. | |
| 4,212,749 | 7/1980 | Kolbe | |
| 4,412,945 | 11/1983 | Takahashi et al. | |
| 4,482,470 | 11/1984 | Reuter et al. | |
| 4,488,981 | 12/1984 | Urfer | 510/405 |
| 4,668,422 | 5/1987 | Malik et al. | 510/135 |
| 4,675,127 | 6/1987 | Kickle et al. | 252/174.17 |
| 4,713,447 | 12/1987 | Letton | 536/18.6 |
| 4,715,991 | 12/1987 | Hirakouchi et al. | |
| 4,732,696 | 3/1988 | Urfer | 510/424 |
| 4,839,098 | 6/1989 | Wisotzki et al. | 510/235 |
| 5,047,167 | 9/1991 | Steyn et al. | 510/403 |
| 5,073,285 | 12/1991 | Liberati et al. | 252/94 |
| 5,100,573 | 3/1992 | Balzer | |
| 5,108,644 | 4/1992 | Machin et al. | 252/174.23 |
| 5,118,439 | 6/1992 | Urfer et al. | |
| 5,242,615 | 9/1993 | Urfer et al. | 510/535 |
| 5,286,406 | 2/1994 | Scholz et al. | 510/158 |
| 5,370,816 | 12/1994 | Balzer et al. | 252/132 |
| 5,464,874 | 11/1995 | Balzer | 514/777 |
| 5,744,441 | 4/1998 | Ufer et al. | 510/433 |
| 5,883,068 | 3/1999 | Hensen et al. | 510/427 |

FOREIGN PATENT DOCUMENTS

91/04313  4/1991  WIPO.

*Primary Examiner*—Yogendra Gupta
*Assistant Examiner*—Christine E. Ingersoll
*Attorney, Agent, or Firm*—John E. Drach; Patrick J. Span

[57] ABSTRACT

A stable, pumpable, flowable and pourable surfactant concentrate, and a method of preparation thereof, said concentrate consisting essentially of (a) at least one anionic or amphoteric surfactant, (b) at least one alkylpolyglycoside surfactant, (c) a viscosity-adjusting agent selected from the group consisting of inorganic and organic electrolytes and (d) water. The concentrate is economically shippable and easily handleable by the formulator for dilution with water, without gelation difficulties, for a variety of end-use applications with adjuvants usually associated with the desired end-use.

42 Claims, No Drawings

# VISCOSITY-ADJUSTED SURFACTANT CONCENTRATE COMPOSITIONS

This application is a continuation of Ser. No. 08/313,652 filed Sep. 26, 1994, now abandoned, which is a continuation of Ser. No. 07/899,561, filed Jun. 16, 1992, now abandoned, which is a continuation-in-part application of Ser. No. 07/644,470 filed Jan. 18, 1991, now U.S. Pat. No. 5,242,615, which is a continuation of Ser. No. 07/406,992 filed Sep. 14, 1989, now abandoned.

BACKGROUND OF THE INVENTION

1. Field of the Invention

The invention herein relates to a viscosity-adjusted surfactant concentrate composition, particularly to a flowable, pumpable, stable surfactant concentrate consisting essentially of a mixture of an alkylpolyglycoside surfactant, an anionic or amphoteric surfactant and an effective amount of a viscosity-adjusting agent.

As indicated in U.S. Ser. No. 07/406,992 noted above, anionic surfactants and amphoteric surfactants are known materials. In a manufacturing or shipping operation it is desirable in handling the surfactants that they be flowable, pumpable and stable at a viscosity to avoid difficulty in processing or shipping the compositions. However, at high concentrations of the anionic or amphoteric surfactants (above 25, and higher, 30 or 40% to about 80% concentrations by weight in water) the viscosity rapidly increases and forms gels. Accordingly, it has been necessary to provide low viscosities for processing and shipping that the solutions of the anionic or amphoteric surfactant be very dilute or have added thereto, agents which reduce the viscosity. Very dilute solutions are objectionable and undesirable from a shipping standpoint, as a large amount of water results in high freight and shipping costs which must be borne by the customer.

It is accordingly important and desirable that a means be provided for preparing highly concentrated compositions in water of anionic or amphoteric surfactants which are flowable, pumpable, pourable and stable on storage.

2. Statement of Related Art

Alcohols, such as ethanol, have been employed in attempts to reduce the viscosity. However, alcohols introduce a flammability problem requiring additional precautions and care in handling.

U.S. Pat. No. 4,488,981 discloses that the addition of alkyl mono and polyglucosides having alkyl groups with six (6) carbon atoms or less in the alkyl group, to aqueous liquid detergents mixtures of anionic or anionic and nonionic surfactants in water reduces the viscosity of the mixture. The patent discloses in Table III, that highly viscous, unpourable gels are obtained in water with no additive and also illustrates the use of ethyl alcohol to provide a highly fluid, easily pourable detergent. With a higher alkyl (8 to 20 carbon) polyglycoside the mass remains a highly viscous, unpourable mass. The anionic surfactants include the sulfates, sulfonates, carboxylates and phosphates, while the nonionic surfactants are the ethoxylated alcohols, phenols, carboxylic esters or amides.

It is also known that the addition of alkylpolyglycosides to a phosphate-built aqueous crutcher slurry can reduce the viscosity of the slurry (U.S. Pat. No. 4,675,127). U.S. patent application Ser. No. 07/260,646 discloses that the addition of an alkylpolyglycoside and an alkali metal chloride to a carbonate containing crutcher slurry, reduces the viscosity of the slurry. A crutcher slurry is a mixture containing minor amounts of surfactant materials and large amounts of detergent builders and fillers. Thus, a crutcher slurry is not a concentrate consisting essentially of surfactants, but rather a slurry of particulate material comprising anionic surfactants, builders, fillers and other solid materials which are used in detergent formulations.

On the other hand, U.S. Pat. No. 4,732,696 describes that the addition of an alkyl glycoside and ammonium chloride to an aqueous liquid detergent formulation can increase the viscosity of the formulation. U.S. patent application Ser. No. 07/353,723 discloses that the addition of an alkylpolyglycoside and an alkali metal chloride within a critical range increases the viscosity of certain liquid sulfosuccinate detergent compositions.

Another patent describing an increase in viscosity is U.S. Pat. No. 4,668,422. The patent deals with liquid hand-soap or bubble bath compositions and illustrates the viscosifying effect (viscosity increase) of the addition of a small amount of ammonium chloride to a mixture containing an alkylpolyglycoside, a betaine, and a fatty amine oxide or fatty amide in a composition which contains a water content preferably from about 70 to about 95% with a total solids or non-volatile content of about 5 to about 30, preferably 10 to 20%.

U.S. Pat. No. 4,839,098, discloses a liquid dishwashing detergent consisting essentially of a dialkyl sulfosuccinate and an alkyl glucoside. Viscosity regulators are mentioned generally which include urea, sodium chloride, ammonium chloride, magnesium chloride and sodium citrate, without discussion of the effect thereof. Each of the examples include a substantial amount of an alcohol, such as isopropanol or ethanol, which as noted earlier, has been used to reduce viscosity.

U.S. Pat. No. 3,954,679 describes the use of water-soluble inorganic salts, such as sodium chloride, for viscosity reduction of an alpha-olefin sulfonate detergent composition. At column 13, lines 40–45, the liquid detergents are made thinning the crutcher mix further with an aqueous alcoholic medium (equal parts of ethanol and water) and further including a hydrotrope such as sodium cumene sulfonate. In Example 3 a variety of materials are discussed to be used instead of the halide salt, some of which increase and some of which decrease the viscosity or have little effect on the gelation or viscosity characteristics.

In view of the foregoing, the art described above shows that the addition of materials, such as sodium chloride, is unpredictable. In some cases, dependent on the specific surfactants, end-use applications, other materials required, and the like, the material is used to increase the viscosity and in other circumstances to decrease the viscosity.

DETAILED DESCRIPTION OF THE INVENTION

Other than in the operating examples, or where otherwise indicated, all numbers expressing quantities of ingredients or reaction conditions used herein are to be understood as modified in all instances by the term "about."

It has now been discovered that highly concentrated surfactant compositions may be prepared by mixing an anionic or amphoteric surfactant and an alkylpolyglycoside surfactant with an effective amount of a viscosity-adjustment agent to provide an aqueous surfactant concentrate having a viscosity to provide a flowable, pourable, pumpable and storage stable composition.

By "concentrate" as used herein is meant a composition in which the total concentration of active surfactant (anionic, amphoteric and alkylpolyglycoside) is from about 30% to about 90% by weight, more desirably from about 40 to about 85%, and preferably about 45 to about 80% by weight.

As the viscous, paste-like mixture or gel forms when anionic or amphoteric surfactants are present at concentrations of about 30% by weight and higher, the anionic or amphoteric surfactant will comprise about 30% or more of the surfactant in the composition, with the alkylpolyglycoside surfactant comprising the remainder of the total concentration of surfactant in the composition.

In the parent applications (U.S. Ser. Nos. 07/644,470 and 07/406,992) from which the present application is derived, the alkylpolyglycoside was employed, in combination with an alkali metal chloride to reduce the viscosity of the anionic or amphoteric surfactant composition, in an amount from about 0.1 to about 10% by weight of the total composition of anionic or amphoteric surfactant, water, and the alkylpolyglycoside metal chloride mixtures.

In a preferred embodiment of the present invention, the alkylpolyglycoside surfactant is preferably present in higher amounts than in the parent application noted above, and may comprise up to about 70 of the total active surfactant composition. The ratio by weight of alkylpolyglycoside to anionic or amphoteric surfactant present will preferably be on the order of about 3:1 to about 1:10. Most preferred embodiments of the invention contain a ratio of polyglycoside to anionic or amphoteric surfactant of about 1:1 to about 1.5:1.

The amount of viscosity-adjusting agent employed will be determined by the nature of the surfactants, nature of the viscosity-adjusting agent, and the viscosity which is desired or required, with amounts as low as about 0.1% by weight being effective in some cases with up to about 10% by weight of the total composition being necessary in others. Preferably from about 0.5 to about 5% and most preferably from about 0.75 to about 3 or 4%.

As the resulting concentrate has a high surfactant concentration, the amount of water therein is small resulting in lower freight and shipping costs to the customer. Since the concentrate is flowable and pourable, the customer, generally a formulator, can easily formulate the product for various end-use applications by merely diluting the concentrate to the desired level and adding the adjuvants usually employed for the particular end-use formulation. Since the concentrate need not contain any alcohol, particularly flammable alcohols, such as the lower alkanols (1–4 carbons), the customer need not take extraordinary precautions. In the preferred embodiments of the present invention, the concentrate is accordingly completely free of any monohydric alcohol, such as the lower alkanols; however, small amounts of monohydric alcohols may be present. Further, in another preferred embodiment, dihydric alcohols, such as the glycols, particularly polyethylene glycol, may be present to aid in clarity, as well as some viscosity adjustment.

The anionic surfactants which are employed in a large number of end-use applications, are generally highly irritative to the skin. However, the alkylpolyglycoside surfactants present in the concentrate, particularly when employed in large amounts, i.e. above 10%, and preferably above about 25 or 30% of the active surfactant in the concentrate, renders the formulated products no longer highly irritative to the skin, and accordingly the concentrate finds special utility for formulation into cosmetic, particularly personal skin care products and applications, where mild or non-irritative properties are desirable, such as shampoos, foam baths, hand soaps, hair conditioners, facial cleansers and the like. Thus, the concentrates of the present invention offer formulation ease with the good properties of the anionic and/or amphoteric surfactant and further offering mildness to skin and eyes.

The anionic surfactants include any of the surfactants commonly classified as anionic surfactants. These surfactants include the alkali metal, ammonium and magnesium salts of the alpha olefin sulfonates, alkyl sulfonates, alkyl aryl sulfonates, alkyl aryl ether sulfates, alkyl sulfates, alkyl ether sulfates, sulfated alcohols and sulfated alcohol ethoxylates, taurates, petroleum sulfonates, alkyl naphthalene sulfonates, alkyl sarcosinates and the alkyl sulfosuccinates in which the alkyl group is a long chain 8 to 22, preferably 10–18, carbon atom group and the aryl group is preferably phenyl or naphthyl. Typical surfactants which fall within the above description include sodium lauryl sulfonate, ammonium lauryl sulfonate, ammonium lauryl sulfate, dodecyl benzene sulfonate, sodium lauryl sulfate, sodium laureth sulfate, sodium lauryl ether sulfate, sodium lauryl myristyl sulfate, diethanolamine lauryl sulfate, ammonium salts of sulfated alcohol ethoxylates, sodium cocoyl isethionate, sodium N-methyl-N-oleyl taurate, sodium N-methyl-N-cocoyl taurate, triethanolamine lauryl sulfate, disodium monooleamide PEG-2 sulfosuccinate, petroleum sulfonates sodium salt, alkyl naphthalene sodium sulfonates, sodium lauroyl sarcosinate, and sodium alkyl sulfosuccinate.

The amphoteric surfactants include the betaines, the sultaines, the imidazoline derivatives and the like. Typical amphoteric surfactants include ricinoleamidopropyl betaine, cocamidopropyl betaine, oleyl betaine, stearyl betaine, stearyl amphocarboxy glycinate, sodium lauraminopropionate, cocoamidopropyl hydroxy sultaine, disodium lauryliminodipropionate, tallowiminodipropionate, cocoampho- carboxy glycinate, cocoimidazoline carboxylate, lauric imidazoline monocarboxylate, lauric imidazoline dicarboxylate, lauric myristic betaine, cocoamidosulfobetaine, alkylamidophospho betaine and the like.

The aliphatic polyglycosides (alkylpolyglycosides) are known compositions and can be prepared by the method disclosed in U.S. Pat No. 4,713,447, which is incorporated herein by reference. In commonly assigned, U.S. application Ser. No. 07/774,430, filed Oct. 10, 1991, also incorporated herein by reference, there is described a number of U.S. patents and published European patent applications describing the preparation of alkylpolyglycosides and their end-use applications. In general, these describe a method of preparation comprising the reaction of a reducing saccharide, e.g., an aldose or ketose saccharide, or source thereof, with a long chain (8–18 carbons) alcohol in the presence of an acid catalyst to form a glycoside, commonly referred to as an alkyl glycoside or alkylpolyglycoside. After removal of the residual unreacted alcohol, the product typically contains the monoglycoside of the long chain alcohol as the predominant glycoside molecular species on a mole percentage basis and the various higher degree of polymerization (DP) long chain alcohol polyglycoside species in progressively decreasing mole percentage amounts or proportions principally from DP2 through DP10 glycosides.

In commercial practice, depending on process economics and the properties of the desired alkylpolyglycoside product, a variety of fatty alcohol reactants may be selected for the reaction. These alcohols include mono alcohols, i.e., those having primarily a single alkyl chain, binary alcohol mixtures, i.e., having primarily two different alkyl chains of different carbon chain lengths, and even ternary mixtures.

Binary mixtures of alcohols are available commercially from natural sources as well as synthetic techniques and are employed commercially for the production of the corresponding mixtures of alkylpolyglycosides. Especially important binary alcohol mixtures include the $C_8$–$C_{10}$, $C_{10}$–$C_{12}$, $C_{12}$–$C_{14}$, and $C_{16}$–$C_{18}$ where the alkyl groups are derived from naturally occurring fats and oils. Important ternary mixtures include the $C_{12}$–$C_{14}$–$C_{16}$ or $C_{10}$–$C_{12}$–$C_{14}$ alcohols. The oxo alcohol technology is also employed which provides mixtures containing an odd number of carbon atoms in the alkyl chain, for example an oxo alcohol composed of a mixture of $C_9$, $C_{10}$ and $C_{11}$ alcohols or $C_{12}$ and $C_{13}$ as well. Other synthetic alcohols may be provided by Ziegler Chemistry in which ethylene is added to a triethylaluminum, which is then oxidized to an alkoxide, which is subsequently converted to a mixture of linear alcohols.

The aliphatic polyglycoside surfactants useful in the practice of the present invention are nonionic surfactants of the formula $RO(R_1O)_mG_r$ wherein R, the residue of the alcohol, is an alkyl or alkenyl group having from about 8 to about 22 carbon atoms and preferably from about 10 to 18 carbon atoms. The aliphatic group can be alkyl or alkenyl but is preferably unbranched alkyl. As used in the present invention, the phrase alkylpolyglycoside is intended to encompass both the alkyl and alkenyl polyglycosides. $R_1$ is an alkyl group having 2 or 3 carbon atoms, m is a number from 0 to 10 and preferably 0. When m is 0, the formula for the glycoside product of the reaction of an alcohol and saccharide is then represented by the formula $ROG_r$, where R is as defined above, O is oxygen, G is the residue of a reducing saccharide and r is the average degree of polymerization of the saccharide (DP) resulting from the various mono, di-, tri-, and higher glycoside fractions present in the product and is typically greater than 1, i.e., from about 1.05, to about 3. The monoglycoside fraction would have one saccharide ring, the diglycoside would have 2, the triglycoside would have 3 with the higher glycoside having corresponding more rings, the average of which in the product therefore being typically greater than about 1, generally in the order of about 1.2 to about 2.8, with preferred mixtures at about 1.4 to about 2.5.

The alkylpolyglycoside products represented by the formula above contain a lipophilic group, the R group, and a hydrophilic group, the $OG_r$ group. For detergent surfactant end-use applications, the product preferably has a hydrophilic-lipophilic balance (HLB) of from about 10 to about 16, most preferably about 11 to about 14.

The lipophilic R groups in the alkylpolyglycosides are accordingly derived from alcohols, preferably monohydric, which should contain from about 6 to about 20, preferably about 8 to about 18 carbon atoms, to provide R groups of sufficient length for detergent is surfactant use applications. While the preferred R groups are saturated, aliphatic or alkyl groups, there may be present some unsaturated aliphatic hydrocarbon groups. Thus, the preferred groups are derived from the fatty alcohols derived from naturally occurring fat and oils, such as octyl, decyl, dodecyl, tetradecyl, hexadecyl, octadecyl, oleyl and linoleyl, but R groups may be derived from synthetically-produced Ziegler alcohols or oxo alcohols containing 9, 10, 11, 12, 13, 14, or 15 carbon atoms. The alcohols of naturally occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process, contain both an even and an odd number of carbon atoms such as the $C_9$, $C_{10}$, $C_{11}$ mixtures of which are also available commercially.

The alkylpolyglycosides may contain a single R group derived from an individual single alcohol, or may be derived from commercially available mixtures of alcohols, either naturally occurring or synthetically produced alcohols, to provide a binary or ternary mixture having 2 or more differing alkyl groups. Mixtures of individual single alkylpolyglycosides may be mixed to provide binary or ternary mixtures to result in an average carbon chain length of the alkyl moiety for a desired HLB for a desired end-use application. Similarly mixtures of commercially available binary or ternary alkylpolyglycoside mixtures may be further mixed to reach a predetermined desired average carbon chain length of the alkyl moiety. Thus, in addition to mixtures of single alkyl group polyglycosides, mixtures of binary components such as a $C_8C_{10}$ alkylpolyglycoside may be mixed with another binary mixture component, such as a $C_{12}C_{14}$ or a ternary mixture, such as a $C_{12}C_{14}C_{16}$ polyglycoside, or a $C_9C_{10}C_{11}$ polyglycoside.

In one preferred embodiment of the present invention, mixtures of 2 or more of at least binary components of alkylpolyglycosides, provide particularly desirable concentrate compositions with anionic or amphoteric surfactants.

The saccharides useful for preparing the aliphatic polyglycoside used in the practice of the present invention, are reducing monosaccharides or materials which can form reducing monosaccharides during the process for preparing the polyglycoside composition. The reducing saccharides include hexoses and pentoses. Typical examples of monosaccharides includes glucose, mannose, galactose, fructose, gulose, talose, altrose, allose, idose, arabinose, xylose, ribose, lyxose and the like, as well as materials which are hydrolyzable to form monosaccharides, such as lower alkyl glycosides (e.g., methyl glycoside, ethyl glycoside, propyl glycoside, butyl glycoside, etc.), oligosaccharides (e.g., sucrose, maltose, maltotriose, lactose, sylobiose, malibiose, cellobiose, raffinose, stachyose, etc.) and polysaccharides such as starch. More for reasons of its low cost and ready availability, glucose is a preferred saccharide.

The viscosity-adjusting agents employed in the concentrates of the present invention, generally are inorganic or organic electrolytes. Optionally, a polyethylene glycol may be employed in combination with the inorganic or organic electrolyte as a co-viscosity-adjusting agent. The polyethylene glycol, in addition to functioning as a viscosity-adjusting agent, serves to improve clarity of the concentrate. The inorganic electrolytes include the alkali metal chloride or sulfate salts, such as lithium, potassium or sodium, and the alkaline earth metal salts such as magnesium chloride. The preferred organic electrolytes are carboxylate salts of the alkali metals above, however, the carboxylic acids themselves may be employed. The acids may be monocarboxylic, dicarboxylic or tricarboxylic acids. The preferred salts are the sodium and potassium salts. The carboxylic acids preferred are those containing from 1 to about 6 carbon atoms which may be substituted with hydroxyl groups. The carboxylates which may be employed include the monocarboxylates formate, acetate, propionate, butyrate, and hydroxy substituted monocarboxylate, such as lactate and gluconate; the dicarboxylates such as the succinates and the tricarboxylates such as the citrate. These acids may generally be represented by the formula

$R^1(COOH)_x$ where $R^1$ is H or an aliphatic hydrocarbon group, preferably alkyl, which may be unsubstituted or hydroxy substituted, and x is a whole integer from 1 to 3, and the total number of carbon atoms in the carboxylate may be up to about 18.

The preferred inorganic electrolytes for use in the present invention are sodium or potassium chloride, and the preferred organic carboxylate electrolytes are sodium or potassium acetate, lactate, citrate, succinate or gluconate. In the preferred concentrate composition, a polyethylene glycol will be employed along with the electrolyte to provide clarity as well as further viscosity adjustment.

The concentrate composition of the present invention requires a small but effective amount of the viscosity-adjusting agent. Generally, the viscosity-adjusting agent is present from about 0.1 to about 10% by weight, preferably in the range of from about 0.5 to about 5% by weight and most preferably in the range of from about 0.75% to about 3.0% or 4% by weight of the composition. The amount of the viscosity-adjusting agent included in the composition is dependent upon the particular surfactant and the amount of viscosity adjustment required. Generally, it is preferred to keep the amount of viscosity-adjusting agent in the concentrate as low as possible so that the non-surfactant materials in the concentrate composition is maintained at a low level. However, if the viscosity-adjusting agent is not objectionable in the subsequent use of the concentrate, any amount which aides in the viscosity adjustment, particularly viscosity reduction, is suitable. At higher levels, viscosity-adjusting agents, such as the alkali metal chlorides are known to increase the viscosity of some surfactant mixtures.

The concentrate composition of the present invention consists essentially of the anionic or amphoteric surfactant, the alkyl polyglycoside, the viscosity-adjusting agent and water. The present invention is not intended to be a viscosity-reducing agent for a crutcher slurry as such, since the product consists essentially of the surfactant, the alkyl polyglycoside, some water and the viscosity-adjusting agent. The active surfactant content (alkylpolyglycoside and anionic or amphoteric surfactant) of the concentrate is from about 30% to about 90% by weight, preferably about 40 to about 85% and most preferably about 45 to about 80% by weight. The anionic or amphoteric surfactant will comprise about 30% or more of the surfactant in the concentrate with the alkylpolyglycoside comprising the remainder, up to about 70% of the surfactant in the concentrate. Preferably the ratio by weight of the alkylpolyglycoside to anionic or amphoteric surfactant present will preferably be in the range of about 3:1 to about 1:10, and most preferably about 1:1 to about 1.5:1.

The following examples serve to illustrate, but not limit, the invention. All parts and percentages are by weight unless otherwise noted. In the first four examples, taken from the parent application from which this application is derived, a composition was prepared containing the surfactant and water. A second composition was prepared containing the surfactant, and a viscosity-reducing amount of the alkylpolyglycoside and the alkali metal chloride and water. The viscosities of the various mixtures were measured at 25° C. with a Brookfield viscosimeter using a No. 4 spindle at 10 RPM.

EXAMPLE 1

A composition was prepared containing 43% by weight of a sodium salt of an alpha olefin sulfonate wherein the alpha olefin contained from 14 to 16 carbon atoms. An aqueous mixture of the alpha olefin sulfonate was prepared by mixing 56.8 grams of the surfactant (88% active material) and 58.2 grams of water. The mixture had a viscosity above 50,000 CPS.

A mixture was prepared by mixing 56.8 grams of the surfactant as above, 58.2 grams of water, 2.0 grams of a 50% by weight aqueous solution of APG® 500 (an alkylpolyglucoside with an alkyl group having 12–13 carbon and a degree of polymerization (DP) of 1.4) and 2.5 grams of sodium chloride. The viscosity of the mixture was 14,000 CPS.

EXAMPLE 2

A mixture was prepared containing 38% of a sodium salt of a 12–13 carbon alkyl ether sulfate containing 2 moles of ethylene oxide. The mixture was prepared by mixing 81.6 grams of a 47% active solution of the alkyl ether sulfate with 18.4 grams of water. The viscosity of the mixture was greater than 50,000 CPS.

A mixture was prepared by mixing 81.6 grams of a 47% active solution of the alkyl ether sulfate used above, 18.4 grams of water, 2 grams of a 50% by weight aqueous solution of APG® 500 and 2.5 grams of sodium chloride. The viscosity of the mixture was 4,840 CPS.

EXAMPLE 3

An aqueous mixture was prepared containing 43% by weight of sodium lauryl sulfate. The mixture was prepared by mixing 89.3 grams of an aqueous mixture containing 56% by weight of lauryl sulfate with 25.2 grams of water. The mixture had a viscosity greater than 50,000 CPS.

A second mixture was prepared by mixing 89.3 grams of the aqueous lauryl sulfate mixture having 56% by weight of lauryl sulfate with 25.2 grams of water, 2 grams of a 50% by weight aqueous solution of APG® 500 and 2.5 grams of sodium chloride. The viscosity of the mixture was 16,100 CPS.

EXAMPLE 4

A mixture was prepared containing 63% by weight of the sodium salt of 12–13 carbon alkyl ether sulfate containing 3 moles of EO. The viscosity of the mixture was greater than 50,000 CPS.

A second mixture was prepared containing 100 grams of a 63% by weight solution of the sodium salt of the 12–13 carbon alkyl ether sulfate used above, 2 grams of a 50% by weight aqueous solution of APG® 500 and 2.5 grams of sodium chloride. The viscosity of the mixture was 2,400 CPS.

EXAMPLE 5

This example illustrates the use of viscosity-adjusting agents, other than alkali metal chlorides, such as sodium chloride employed with small amounts of an alkylpolyglycoside for reduction of the viscosity of an anionic surfactant, sodium lauryl sulfate. The composition consisted essentially of 80 grams of sodium lauryl sulfate (Witco 1260), 2.5 grams of APG® 225 (50% active) and 2.5 grams of viscosity-adjusting agent. The results can be seen below:

| Composition | Viscosity (CPS) |
| --- | --- |
| Sulfate alone | 1630 |
| Sulfate + APG | 1380 |
| Sulfate + APG + | |
| (a) sodium citrate | 888 |

-continued

| Composition | Viscosity (CPS) |
|---|---|
| (b) potassium acetate | 53 |
| (c) carboxymethyl oxysuccinate | 654 |

In the examples to follow, the following materials are employed:
1. APG® Surfactant 225—an alkylpolyglycoside in which the alkyl group contains 8 and 10 carbons from a mixture of mixed $C_8$ and $C_{10}$ alkanols, in which the alkyl chain by weight % contains 45% $C_8$ and 55% $C_{10}$, and having an average DP of 1.6, an average lipophile chain (alkyl group), i.e., R equal to 9.1 and an HLB of 13.6.
2. APG® Surfactant 200—an alkylpolyglycoside substantially the same as APG® 225 noted above in which the alkyl chain by weight contains 45% $C_8$ and 55% $C_{10}$ but having an average DP of 1.4.
3. APG® Surfactant 625—an alkyl polyglycoside in which the alkyl groups are a mixture of $C_{12}$, $C_{14}$ and $C_{16}$ chains in a weight ratio respectively of 68:26:6, and having an average DP of 1.6, an average lipophile chain of 12.76 and an HLB of 12.1.
4. APG® Surfactant 600—an alkylpolyglycoside substantially the same as the 625 product above but having an average DP of 1.4 and an HLB of 11.5.
5. APG® Surfactant 400—an alkyl polyglycoside comprised of a mixture of 55.8% of APG® 200 and 33% of APG® 600 and containing 11.2% water.
6. Standapol EA-1—ammonium laureth (1EO) sulfate anionic surfactant.
7. Standamid SD—cocoamide diethanolamine.
8. Standapol ES-1—sodium laureth (1EO) sulfate anionic surfactant.
9. Carbowax 400—polyethylene glycol with a molecular weight of 380–420.

All of the foregoing products are products available from Henkel Corporation except for the Carbowax 400 which is available from Union Carbide Chemicals.

EXAMPLE 6

In this example, these aqueous surfactant concentrates were prepared consisting essentially of an alkylpolyglycoside surfactant, an anionic surfactant and a viscosity-adjusting agent. The samples' composition can be seen from the following Table 1.

TABLE 1

| COMPONENT | 6A (% by wt.) | 6B (% by wt.) | 6C (% by wt.) |
|---|---|---|---|
| Potassium Acetate | 4.00 | 4.00 | 4.00 |
| Potassium Chloride | 1.00 | 1.00 | 1.00 |
| APG ® 400 (50%) | 12.50 | 25.00 | 37.50 |
| APG ® 625 (50%) | 37.50 | 25.00 | 12.50 |
| Standapol EA-1 (70%) | 34.20 | 34.20 | 34.20 |
| Water | q.s.* to 100% | | |
| Viscosity (CPS) | 1500 | 1750 | 2450 |
| Appearance | hazy | hazy | hazy |

*q.s. = quantity sufficient

When the products are diluted to 20%, the viscosities of samples 6A 6B and 6C were 100, 80 and 20 CPS respectively.

The samples were evaluated in a foam test in diluted foam to which was added Standamid SD, the diluted composition being as shown in Table 2. The foam test was conducted following the "Foam Test Methodology" described below with artificial sebum. The viscosity of each sample was determined without and with the further addition of sodium chloride.

Foam Test Methodology

Prepare a 10% aqueous solution of product being evaluated. In the results which follow 0.5 g. synthetic sebum, the composition of which follows below, was added to 50.0 g. product prior to preparing the 10% aqueous solution. Four (4) grams of this solution was added to 146 grams of water (hardness 50 ppm) heated to 29° C.±1° C. and agitated for five (5) seconds in a Sears electronic blender with microprocessor control, medium/No. 5 speed agitation. The foam is transferred into a 500 ml graduated cylinder and the initial foam volume measured to the nearest 5 ml and then the position of the foam/water interface is recorded after 3.5 minutes. This later reading represents the foam drainage.

| SYNTHETIC SEBUM COMPOSITION | |
|---|---|
| Ingredient | % W/W |
| Palimitic Acid | 10.00 |
| Stearic Acid | 5.00 |
| Coconut Oil | 15.00 |
| Paraffin | 10.00 |
| Spermacetti | 15.00 |
| Olive Oil | 20.00 |
| Squalene | 5.00 |
| Cholesterol | 5.00 |
| Oleic Acid | 10.00 |
| Linoleic Acid | 5.00 |
| | 100.00 |

TABLE 2

| | Foam Samples | | |
|---|---|---|---|
| | 6A-1 | 6B-1 | 6C-1 |
| Water | 73.0 | 73.0 | 73.0 |
| Composition 6A | 24.0 | — | — |
| Composition 6B | — | 24.0 | — |
| Composition 6C | — | — | 24.0 |
| Standamid SD | 3.0 | 3.0 | 3.0 |
| Foam: | 255/135 | 270/135 | 280/135 |
| Viscosity (no added NaCl) | 9100 | 3500 | 1200 |
| 0.50% NaCl | 6500 | 4350 | 1950 |
| 1.00% NaCl | 3500 | 3500 | 2300 |
| 1.50% NaCl | 1250 | 2250 | 2500 |

EXAMPLE 7

The same concentrate formulations as in Samples 6B and 6C were prepared except that the amounts of potassium acetate and potassium chloride were 2% of each. The samples designated here as 7A and 7B, had a pH of a 10% solution of 6.2 and 6.4 respectively. Solutions were prepared containing 73% water, 24% of the sample, 3% of Standamid SD and viscosities determined without and with further addition of sodium chloride. The results can be seen from the following Table 3.

TABLE 3

| | Viscosity (CPS) | | | | |
| --- | --- | --- | --- | --- | --- |
| | NaCl Addition (%) | | | | |
| SAMPLE | 0 | 0.5 | 1.0 | 1.5 | 2.0 |
| 7A | 3300 | 3400 | 3600 | 4000 | 4500 |
| 7B | 1100 | 1800 | 2000 | 2100 | 2300 |

EXAMPLE 8

Samples were prepared employing a variety of viscosity-adjusting agents. The samples' compositions and preparations can be seen from the following Table 4.

TABLE 4

| | Samples | | | | |
| --- | --- | --- | --- | --- | --- |
| COMPONENT | 8A (wt %) | 8B (wt %) | 8C (wt %) | 8D (wt %) | 8E (wt %) |
| Sodium sulfate | 3.0 | — | — | 3.0 | 3.0 |
| Potassium chloride | — | 2.0 | — | — | — |
| Sodium Acetate | — | 2.0 | — | — | — |
| Sodium chloride | — | — | 2.0 | — | — |
| Potassium acetate | — | — | 3.0 | — | — |
| APG ® 400 (50%) | 25.0 | 25.0 | 25.0 | 25.0 | 12.50 |
| APG ® 625 (50%) | 25.0 | 25.0 | 25.0 | 25.0 | 37.50 |
| Carbowax 400 | — | — | — | 1.0 | — |
| Standapol EA-1 (70%) | 34.2 | 34.2 | 34.20 | 34.20 | 34.20 |
| Water | q.s. to 100% | | | | |
| pH (10% solution): | 6.5 | 6.5 | 6.5 | 6.5 | 6.5 |
| Viscosity (CPS): | 11600 | 6000 | 3100 | 3200 | 10000 |
| Appearance: | clear viscous liquid | slight hazy liquid | slight hazy liquid | clear viscous liquid | hazy liquid |

*q.s. = quantity sufficient

A viscosity profile was conducted on sample 8A, 8B, 8C and 8D with varying amounts of NaCl on a sample of 24 parts of the compositions above, 3.0 parts Standamid SD and 73 parts water. The results are seen in Table 5 below.

TABLE 5

| | Viscosity (CPS) | | | |
| --- | --- | --- | --- | --- |
| % NaCl | 8A | 8B | 8C | 8D |
| 0 | 1100 | 1650 | 2650 | 700 |
| 0.5 | 2550 | 2850 | 3950 | 2500 |
| 1.0 | 4200 | 3250 | 4100 | 3500 |
| 1.5 | 3700 | 2450 | 3450 | 3650 |

EXAMPLE 9

A sample was prepared following the surfactant composition of 6B except that only potassium chloride was used as the viscosifying agent at a level of 3%. The pH of a 10% solution was 6.45, the viscosity was 4550 cps and the product was a hazy liquid. Upon the addition of Carbowax 400 the product was a clear liquid with a viscosity of 4300 cps.

The product was evaluated with varying amounts of NaCl at a 10% active solution with 3% Standamid SD and a 12% active solution with 3% Standamid SD. The results can be seen in Table 6 below.

TABLE 6

| | Viscosity (cps) at 25° C. | |
| --- | --- | --- |
| % NaCl | 10% solution | 12% solution |
| 0 | 500 | 2000 |
| 0.5 | 1850 | 3400 |
| 1.0 | 2650 | 3700 |
| 1.5 | 2460 | 2450 |
| 2.0 | 2000 | 2000 |

EXAMPLE 10

In this example, samples were prepared, again using 50% active solution of the alkylpolyglycosides and 70% active solution of the ethoxylated alkyl sulfate. Carbowax 400 was included in each sample formulation to assist in providing a clear solution as well as some reduction in viscosity. The compositions and properties can be seen from the following Table 7.

TABLE 7

| | Samples | | |
| --- | --- | --- | --- |
| Component | 10A | 10B | 10C |
| APG ® 400 (50%) | 25.0 | 25.0 | 25.0 |
| APG ® 625 (50%) | 25.0 | 25.0 | 25.0 |
| Standapol EA-1 (70%) | 34.2 | 34.2 | 34.2 |
| Sodium Sulfate | — | — | 2.0 |
| Carbowax 400 | 1.0 | 1.0 | 1.0 |
| Sodium Citrate | 2.0 | 2.0 | 2.0 |
| Potassium Chloride | 1.0 | — | — |
| Sodium Chloride | — | 1.0 | — |
| Water | q.s. to 100% | | |
| pH (10% solution) | 6.4 | 6.4 | 6.4 |
| Viscosity (cps) | 7900 | 8500 | 8500 |
| Cloud Point | +15° C. | +12° C. | +12° C. |

The samples were evaluated at both 10% active and 12% active solutions each containing 3% Standamid SD. These results can be seen in Table 8 below.

TABLE 8

| | Viscosity (cps) | | | | | |
| --- | --- | --- | --- | --- | --- | --- |
| | 10% solution | | | 12% solution | | |
| | 10A | 10B | 10C | 10A | 10B | 10C |
| 0 | 300 | 250 | 400 | 850 | 800 | 900 |
| 0.5 | 1750 | 1450 | 1650 | 2450 | 2550 | 2500 |
| 1.0 | 2600 | 2250 | 3100 | 3720 | 3350 | 4100 |
| 1.5 | 2500 | 3250 | 3300 | 4100 | 3500 | 3650 |
| 2.0 | 2350 | 2550 | 2550 | 3000 | 3100 | 3500 |

All the systems provide adequate viscosity profiles.

EXAMPLE 11

In this example, samples were prepared employing sodium lactate as a viscosity-adjusting agent. Samples 11A and 11C were evaluated at 10% and 12% active solutions containing Standamid SD. The results can be seen in Tables 9 and 10 below.

TABLE 9

| Component | Sample | | |
|---|---|---|---|
| | 11A | 11B | 11C |
| APG 400 (50%) | 25.0 | 25.0 | 25.0 |
| APG 625 (50%) | 25.0 | 25.0 | 25.0 |
| Standapol EA-1(70%) | 34.2 | 34.2 | 34.2 |
| Sodium sulfate | — | — | 2.0 |
| Carbowax 400 | 1.0 | 1.0 | 1.0 |
| Sodium lactate | 2.0 | 2.0 | 3.0 |
| Potassium chloride | 1.0 | — | — |
| Sodium chloride | — | 1.0 | — |
| Water | q.s. to 100% | | |
| pH (10% solution) | 6.4 | 6.4 | 6.4 |
| Viscosity (cps) | 8600 | 9800 | 8800 |
| Cloud Point | +16° C. | — | +14° C. |

TABLE 10

| | Viscosity (cps) | | | |
|---|---|---|---|---|
| | 10% solution | | 12% solution | |
| % NaCl | 11A | 11C | 11A | 11C |
| 0 | 250 | 250 | 800 | 750 |
| 0.5 | 1850 | 750 | 2450 | 2450 |
| 1.0 | 2750 | 2700 | 4500 | 4350 |
| 1.5 | 3150 | 3100 | 3700 | 3200 |
| 2.0 | 2400 | 2500 | 2850 | 2400 |

Both of the samples exhibit adequate viscosity profiles.

EXAMPLE 12

In this example, the inclusion of sodium lactate at a 3.0% level was evaluated. The composition and evaluation of sample 12A can be seen from the following tables.

TABLE 12A

| Component | Sample | |
|---|---|---|
| | 12A | 12B |
| APG 400 (50%) | 25.0 | 25.0 |
| APG 625 (50%) | 25.0 | 25.0 |
| Standapol EA-1 (70%) | 34.2 | 34.2 |
| Sodium lactate | 3.0 | 3.0 |
| Potassium chloride | 1.0 | — |
| Sodium chloride | — | 1.0 |
| Carbowax 400 | 1.0 | 1.0 |
| Water | q.s. to 100% | |
| pH (10% solution): | 6.4 | 6.4 |
| Viscosity (cps): | 5750 | 6000 |
| Cloud Point: | +10° C. | +15° C. |

TABLE 12B

| | Viscosity (cps) | |
|---|---|---|
| | 10% solution | 12% solution |
| % NaCl | 11A sample | 11A sample |
| 0 | 425 | 950 |
| 0.5 | 2300 | 2950 |
| 1.0 | 3250 | 4200 |
| 1.5 | 3000 | 4350 |
| 2.0 | 2100 | 3000 |

Formulation A, in particular, gave a very good viscosity response. Both of the products have an advantage in the use of sodium lactate in that it is a liquid. The cloud point of sample 12A was lower than sample B. The compositions are flowable, pourable and pumpable.

EXAMPLE 13

In this example, the proportion of ratios of alkylpolyglycosides and ether sulfate anionic surfactant were raised, employing the same amounts of viscosity-adjusting agents sodium lactate, potassium chloride and polyethylene glycol as in sample 12A. The composition and properties can be seen in Tables 13 below.

TABLE 13A

| Component | Sample 12A |
|---|---|
| APG ® 400 (50%) | 20.0 |
| APG ® 625 (50%) | 20.0 |
| Standapol EA-1 (70%) | 41.0 |
| Carbowax 400 | 1.0 |
| Potassium chloride | 1.0 |
| Sodium lactate | 3.0 |
| Water | 14.0 |
| | 100.0% |
| pH (10% solution): | 6.4 |
| Viscosity (cps) | 6100 |
| Appearance: | slight haze |

TABLE 13B

| | Viscosity (cps) on 12A sample | |
|---|---|---|
| % NaCl | 10% solution | 12% solution |
| 0 | 350 | 1000 |
| 0.5 | 1900 | 4450 |
| 1.0 | 4300 | 5800 |
| 1.5 | 4100 | 6500 |
| 2.0 | 3200 | 4000 |

The viscosity response was very good to provide a flowable, pumpable and pourable product.

As is illustrated by the foregoing examples, compositions are provided which possess a viscosity which results in pourability, flowability and pumpable properties, so that the products can be easily handled in manufacture and by the consumer who will formulate the composition for desired end-use applications. Thus, the product dilutes in water very rapidly without gelation or large increases in viscosity and is accordingly easily formulated into cleaning products where good foam and viscosity potentiation is desired. The products are stable and economically shippable as they contain desirably low amounts of water. With the presence of the alkylpolyglycosides, the product is less irritating to the skin than the use of anionic surfactants alone, thus providing end-use formulation particularly useful for mild personal skin care products.

A preferred concentrate is one containing about 50% total active surfactant consisting essentially of the following typical composition:

| Anionic or amphoteric surfactant | 25% active |
|---|---|
| Alkylpolyglycoside | 25% active |
| Viscosity-adjusting agent | 1–5% |
| Water | Balance to 100% |

The alkylpolyglycoside is preferably a mixture of 2 or more alkylpolyglycosides of varying average alkyl moieties, such as mixtures of the APG® 400 and APG® 625 exemplified herein. The anionic surfactant are preferred, such as the long chain alkyl ($C_8$ to $C_{18}$) sulfates or sulfonates, ethoxylated or unethoxylated, exemplified above as sodium laureth (EO-1) sulfate, or ammonium laureth sulfate. The ratio by weight of alkylpolyglycosides to anionic surfactant is preferably about 1:1 but may vary from about 0.65:1 to about 1.5:1. The viscosity-adjusting agents are preferably organic carboxylates such as the acetate, lactate or citrate, the lactate having an advantage in being liquid and posing no undesirable odor, which may be encountered with the acetate. The preferred inorganic electrolytes are potassium chloride, sodium chloride, sodium sulfate. Mixture of the organic carboxylate electrolytes and the inorganic electrolytes are typically employed and polyethylene glycol is a preferred agent for use in admixture with the organic carboxylate electrolytes and the inorganic electrolytes. The viscosity-adjusting agents are preferably employed in an amount from about 1 to about 5%, with about 1 to 3 or 4% being most preferred. As seen in the examples, the concentrates will have a viscosity (Brookfield) measured at 25° C. of below about 16000 centipoise (cps), more desirably below about 10000 cps, and preferably below about 5000 cps, with some samples between about 1000–3000 cps. Upon dilution to about 10%, and with further addition of NaCl, the samples remain at low viscosity, preferably below 5000 cps without gelation.

As indicated earlier above, the concentrate is useful in formulating various end-use applications, particularly personal care products. Accordingly, a method of preparing end-use formulations is provided which comprises mixing the concentrates described herein with the usual adjuvants associated with the particular end-use application. Thus, the end-use compositions may contain in addition to the concentrate components, other co-surfactants, detergency builders, soil-suspending agents, brightening agents, abrasives, dyes, fabric-conditioning agents, hair-conditioning agents, hydrotropes, anti-microbial agents, solvents, fillers, etc. Such materials assist the alkylpolyglycoside, and anionic or amphoteric surfactant present in the concentrate, in its end-use application are accordingly auxiliary, optional, reagents referred to herein as "adjuvants."

As indicated, because of the mildness resulting from the association of the alkylpolyglycoside with the normally irritative anionic surfactants, the concentrates find particular utility in formulating personal care products, such as shampoos, foam baths, facial cleansers, liquid soaps, soap bars, toothpaste, mouthwashes, antiperspirants, cleansing towelettes, and the like. While the present invention is directed to the concentrates from which the end-use applications are formulated, and only indirectly involved with end-use formulations, the following illustrate various end-use formulations in the personal care area.

FORMULATION A
MILD SHAMPOO WITH ALKYLPOLYGLYCOSIDE

| INGREDIENTS | % WT/WT |
|---|---|
| STANDAPOL SH-124-3 (1) (Disodium Laureth Sulfosuccinate) | 19.6 |
| Alkylpolyglycoside (1) | 12.0 |
| STANDAMOX LAO-30 (1) (Lauramine Oxide) | 1.5 |

-continued

FORMULATION A
MILD SHAMPOO WITH ALKYLPOLYGLYCOSIDE

| INGREDIENTS | % WT/WT |
|---|---|
| STANDAMID SD (1) (Cocamide DEA) | 1.5 |
| Germaben II | 0.25 |
| Citric Acid | To pH6.0 |
| Sodium Chloride | To desired viscosity |
| Water, Fragrance | q.s. to 100 |

(1) Product of Henkel Corp.

FORMULATION B
LOW IRRITATION SHAMPOO

| INGREDIENTS | % WT/WT |
|---|---|
| Water | 54.95 |
| TEXAPON ASV (1) (Sodium Laureth Sulfate (and) Magnesium Laureth Sulfate (and) Sodium Laureth-8 Sulfate (and) Magnesium Laureth-8 Sulfate (and) Sodium Oleth Sulfate (and) Magnesium Oleth Sulfate) | 33.00 |
| Alkylpolyglycoside (1) | 6.00 |
| CETIOL HE (1) (PEG-7 Glyceryl Cocoate) | 1.00 |
| STANDAMID SD (1) (Cocamide DEA) | 3.00 |
| Kathon CG (2) | 0.05 |
| Sodium Chloride | 2.00 |
| Dyes and Fragrance | q.s. |
| | 100.00 |

(1) Product of Henkel Corp.
(2) Product of Rohm & Haas

FORMULATION C
HIGH PERFORMANCE LOW IRRITATION SHAMPOO

| INGREDIENT | % WT/WT |
|---|---|
| Alkylpolyglycoside (1) | 15.0 |
| STANDAPOL EA-2 (1) (Ammonium Laureth Sulfate) | 15.0 |
| VELVETEX BK-35 (1) Cocamidopropyl Betaine) | 12.5 |
| NUTRILAN I (1) (Hydrolyzed Collagen) | 1.5 |
| Citric Acid | to pH6.0–6.5 |
| Fragrance | q.s. |
| Water, Preservative | balance |

(1) Product of Henkel Corp.

FORMULATION D
LOW IRRITATION FACIAL CLEANSER

| INGREDIENT | % WT/WT |
|---|---|
| Water | q.s. to 100% |
| TEXAPON ASV (1) (Sodium Laureth Sulfate (and) Magnesium Laureth | 12.50 |

FORMULATION D
LOW IRRITATION FACIAL CLEANSER

| INGREDIENT | % WT/WT |
| --- | --- |
| Sulfate (and) Sodium Laureth-8 Sulfate (and) Magnesium Laureth-8 Sulfate (and) Sodium Oleth Sulfate (and) Magnesium Oleth Sulfate) | |
| Alkylpolyglycoside (1) | 6.40 |
| VELVETEX CDC (1) (Cocamphocarboxyglycinate) | 5.00 |
| LAMEPON S (1) (Potassium Coco Hydrolyzed Animal Protein) | 5.00 |
| Citric Acid to pH 5.5–6.0 | |
| Kathon CG (2) | 0.05 |
| Fragrance | 0.20 |
| Dyes | q.s. |
| EUPERLAN PK-810 (1) (Glycol Distearate (and) Sodium Laureth Sulfate (and) Cocamide MEA (and) Laureth-9) | 3.00 |

(1) Product of Henkel Corp., Emery Group, Ambler, PA
(2) Product of Rohm & Haas, Philadelphia, PA

FORMULATION E
CONDITIONING SHAMPOO

| Ingredients | % W/W |
| --- | --- |
| Water | 47.80 |
| STANDAPOL ES-2 (1) (Sodium Laureth Sulfate) | 36.00 |
| Alkylpolyglycoside (1) | 6.00 |
| VELVETEX BA-35 (1) (Cocamidopropyl Betaine) | 3.00 |
| DEHYQUART E (1) (Hydroxycetyl Hydroxyethyl Dimonium Chloride) | 2.00 |
| AETHOXAL B (1) (PPG-5-Laureth-5) | 1.00 |
| EUPERLAN PK-810 (1) (Glycol Distearate (and) Sodium Laureth Sulfate (and) Cocamide MEA (and) Laureth-9 | 3.00 |
| Sodium Chloride | 1.00 |
| Kathon CG (2) | 0.05 |
| Fragrance U-8210 (3) | 0.1 |
| | 100.00 |

(1) Product of Henkel Corp., Emery Group, Ambler, PA
(2) Product of Rohm & Haas, Philadelphia, PA
(3) Product of Shaw Mudge & Co., Stamford, CT

FORMULATION F
LOW IRRITATION FOAM BATH/BODY SHAMPOO

| Ingredients | % W/W |
| --- | --- |
| Water | 30.45 |
| STANDAPOL SH-124-3 (1) (Disodium Laureth Sulfosuccinate) | 40.00 |
| Alkylpolyglycoside (1) | 12.00 |
| LAMEPON S (1) (Potassium Coco-Hydrolyzed Animal Protein) | 9.00 |
| STANDAMID LDO (1) (Lauramide DEA) | 3.00 |
| STANDAMOX LAO-30 (1) (Lauramine Oxide) | 3.00 |
| CETIOL HE (1) (PEG-7 Glyceryl Cocoate) | 0.50 |
| Kathon CG (2) | 0.05 |
| Sodium Chloride | 2.00 |
| Fragrance and dyes | q.s. |
| | 100.00 |

(1) Product of Henkel Corp., Organic Prod. Div., Ambler, PA
(2) Product of Rohm & Haas, Philadelphia, PA

FORMULATION G
MILD SHOWER CLEANSER

| Ingredients | % W/W |
| --- | --- |
| Water | 62.60 |
| STANDAPOL ES-3 (1) (Sodium Laureth Sulfate) | 10.50 |
| Alkylpolyglycoside (1) | 12.00 |
| LAMEPON S (1) (Potassium Coco-Hydrolyzed Animal Protein) | 9.00 |
| CETIOL HE (1) (PEG-7 glyceryl Cocoate) | 0.50 |
| EUPERLAN PK-810 (1) (Glycol Distearate (and) Sodium Laureth Sulfate (and) Cocamide MEA (and) Laureth-9) | 3.00 |
| Propylene Glycol | 1.00 |
| COSMEDIA GUAR C-261N (1) (Guar Hydroxypropyl Trimonium Chloride) | 0.75 |
| Sodium Chloride | 0.50 |
| Kathon CG (2) | 0.05 |
| Fragrance | 0.10 |
| | 100.00 |

(1) Product of Henkel Corp.
(2) Product of Rohm & Haas

FORMULATION H
CLEANSING TOWELETTE

| Ingredients | % W/W |
| --- | --- |
| Water | q.s. to 100 |
| STANDAPOL SH-124-3 (1) (Disodium Laureth Sulfosuccinate) | 5.00 |
| Alkylpolyglycoside (1) | 3.00 |
| CETIOL HE (1) (PEG-7 Glycereth Cocoate) | 0.50 |
| ETHOXYLAN 1686 (1) | 0.50 |
| Kathon CG (2) | 0.05 |
| Fragrance | 0.10 |
| | 100.00 |

(1) Product of Henkel Corp.
(2) Product of Rohm & Haas

What is claimed is:

1. A method of preparing a highly concentrated flowable, pumpable, pourable, and stable surfactant concentrate of a mixture consisting essentially of at least one anionic or amphoteric surfactant and at least one alkylpolyglycoside surfactant of the formula $RO(R_1O)_mG_r$ wherein R is an alkyl or alkenyl group having from about 8 to about 22 carbon atoms, $R_1$ is an alkyl group having 2 or 3 carbon atoms, m is a number of from 0 to 10, G is the residue of a reducing saccharide and r is the average degree of polymerization and is a number from 1.4 to about 3, wherein the alkylpolyglycoside surfactant therein comprises at least two alkylpolyglycosides of two different average alkyl chain moieties comprising adding to said mixture a viscosity-adjusting amount of a viscosity-adjusting agent selected from the group consisting of inorganic and organic electrolytes, and mixing said anionic or amphoteric surfactant, said alkylpolyglycoside surfactant and said viscosity-adjusting agent with water to provide an aqueous, stable, concentrate having a viscosity level at which the concentrate is flowable, pumpable and pourable and in which the total surfactant is about 30 to about 90% by weight of the concentrate, and the anionic or amphoteric surfactant comprises about 30% by weight of the total surfactant in said concentrate, with the alkylpolyglycoside surfactant being the remainder up to about 70% of the total surfactant in said concentrate and the ratio by weight of the alkylpolyglycoside surfactant to anionic or amphoteric surfactant is from 3:1 to about 1:10.

2. A method as defined in claim 1, wherein the amount of viscosity-adjusting agent is from about 0.1 to 10% by weight of the concentrate composition.

3. A method as defined in claim 2, wherein the amount of viscosity-adjusting agent is from about 0.5 to about 5%.

4. A method as defined in claim 3, wherein the amount of viscosity-adjusting agent is about 0.75 to about 4%.

5. A method as defined in claim 1 wherein said viscosity-adjusting agent is an inorganic electrolyte selected from the group consisting of of alkali metal or alkaline earth metal salts of a mineral acid.

6. A method as defined in claim 5, wherein the metal salt is a chloride or sulfate salt of sodium or potassium.

7. A method as defined in claim 1 wherein said viscosity-adjusting agent is an organic electrolyte of an organic carboxylic acid of the formula $R^1(COOH)_x$ where $R^1$ is H or an aliphatic hydrocarbon group, unsubstituted or hydroxy substituted, x is a whole integer from 1 to 3, and the total number of carbon atoms is up to about 18.

8. A method as defined in claim 7, wherein said viscosity-adjusting agent is an alkali metal salt of a carboxylic acid selected from the group consisting of formic acid, acetic acid, propionic acid, butyric acid, lactic acid, gluconic acid, succinic acid and citric acid.

9. A method as defined in claim 1 wherein the alkylpolyglycoside surfactant present in the concentrate has a hydrophilic-lipophilic balance of about 10 to about 16.

10. A method as defined in claim 9, wherein one of the alkylpolyglycoside surfactants is a polyglycoside having a mixed $C_8C_{10}$ alkyl moiety.

11. A method as defined in claim 9, wherein one of the alkylpolyglycoside surfactants is a polyglycoside having a mixed $C_{12}C_{14}C_{16}$ alkyl moiety.

12. A method as defined in claim 1 wherein said anionic surfactant comprises at least one salt selected from the group consisting of salts of alkyl sulfates, alkyl sulfonates, alkyl aryl sulfonates, alkyl ether sulfates, alpha olefin sulfonates, alkyl aryl ether sulfates, sulfated alcohols and ethoxylated sulfated alcohols, taurates, petroleum sulfonates, alkyl naphthalene sulfonates, alkyl sarcosinates and alkyl sulfosuccinates in which the alkyl group contains from about 8 to about 22 carbon atoms and the aryl group is phenyl or naphthyl.

13. A method as defined in claim 12 wherein said anionic surfactant is a sodium, ammonium or magnesium salt of an alkyl sulfate or ethoxylated alkyl sulfate in which the alkyl group contains from about 8 to about 18 carbon atoms and the number of ethoxylate groups is from 1 to about 8.

14. A method as defined in claim 13 wherein said anionic alkyl sulfate surfactant is sodium or ammonium lauryl sulfate and said anionic ethoxylated alkyl sulfate is sodium, ammonium or magnesium laureth sulfate or oleth sulfate.

15. A method as defined in claim 1, wherein said amphoteric surfactant comprises a betaine, sultaine, aminopropionate or imidazoline derivative.

16. A method of preparing a highly concentrated flowable, pumpable, pourable and stable surfactant concentrate of a mixture of at least one anionic surfactant and at least one alkylpolyglycoside surfactant comprising adding to said mixture a viscosity-adjusting agent selected from the group consisting of inorganic and organic electrolytes and mixing said anionic surfactant, said alkylpolyglycoside surfactant and said viscosity-adjusting agent with water to provide an aqueous, stable concentrate having a viscosity level at which the concentrate is flowable, pumpable and pourable and wherein the total surfactant present in said concentrate is from about 30% to about 90% by weight of said concentrate and said anionic surfactant comprises at least about 30% by weight of the total surfactant present and the ratio of alkylpolyglycoside surfactant to anionic surfactant is from 3:1 to about 1:1 and wherein said anionic surfactant is a sodium, ammonium or magnesium salt of an alkyl sulfate or ethoxylated alkyl sulfate in which the alkyl group contains from about 8 to about 22 carbon atoms and said alkylpolyglycoside surfactant has the formula $ROG_r$ where R is an alkyl group having from about 8 to about 22 carbon atoms, O is oxygen, G is the residue of a reducing saccharide and r is a number from 1.4 to about 3, and wherein the alkylpolyglycoside surfactant comprises at least two alkylpolyglycosides of two different average alkyl chain moieties.

17. A method as defined in claim 16, wherein said inorganic electrolyte is a chloride or sulfate salt of sodium or potassium and said organic electrolyte is a sodium or potassium salt of an organic carboxylic acid selected from the group consisting of acetic acid, propionic acid, lactic acid, succinic acid and citric acid.

18. A method as defined in claim 16, wherein said concentrate further comprises a polyethylene glycol added to said mixture as an additional viscosity-adjusting agent.

19. A method as defined in claim 18, wherein said polyethylene glycol has a molecular weight of about 400.

20. A stable, pumpable, flowable and pourable surfactant concentrate prepared by the method of claim 1.

21. A stable, pumpable, flowable and pourable surfactant concentrate prepared by the method of claim 16.

22. A stable, pumpable, flowable and pourable surfactant concentrate consisting essentially of (a) at least one anionic or amphoteric surfactant;

(b) at least one alkylpolyglycoside surfactant of the formula $ROG_r$ where R is an alkyl or alkenyl group having from about 8 to about 22 carbon atoms, O is oxygen, G is the residue of a reducing saccharide and r is the average degree of polymerization and is a number of from 1.4 to about 3;

(c) an effective amount of a viscosity-adjusting agent selected from the group consisting of inorganic and organic electrolytes; and (d) water;

wherein the total surfactant (a) and (b) present in the concentrate is from about 30% to about 90% by weight of the total surfactant in the concentrate and the anionic or amphoteric surfactant (a) comprises at least 30% of the total surfactant in said concentrate with the alkylpolyglycoside surfactant (b) being the remainder up to about 70% by weight of the total surfactant in said concentrate, and the ratio by weight of the alkylpolyglycoside surfactant (b) to surfactant (a) is from about 3:1 to about 1:1 and wherein the alkyl polyglycoside surfactant comprises at least two alkylpolyglycosides of two different average alkyl chain moieties.

23. A concentrate as defined in claim 22 wherein the amount of viscosity-adjusting agent is from about 0.1 to 10% by weight of the concentrate composition.

24. A concentrate as defined in claim 23, wherein the amount of viscosity-adjusting agent is from about 0.5 to about 5%.

25. A concentrate as defined in claim 24, wherein the amount of viscosity-adjusting agent is about 0.75 to about 4%.

26. A concentrate as defined in claim 22 wherein a polyethylene glycol is added to said mixture as an additional viscosity-adjusting agent.

27. A concentrate as defined in claim 26 wherein said polyethylene glycol has a molecular weight of about 400.

28. A concentrate as defined in claim 22 wherein said viscosity-adjusting agent is an inorganic electrolyte selected from the group consisting of of alkali metal or alkaline earth metal salts of a mineral acid.

29. A concentrate as defined in claim 28 wherein the metal salt is a chloride or sulfate salt of sodium or potassium.

30. A concentrate as defined in claim 22 wherein said viscosity-adjusting agent is an organic electrolyte of an organic carboxylic acid of the formula $R^1(COOH)_x$ where $R^1$ is H or an aliphatic hydrocarbon group, unsubstituted or hydroxy-substituted, x is a whole integer from 1 to 3, and the total number of carbon atoms is up to about 18.

31. A concentrate as defined in claim 30 wherein said viscosity-adjusting agent is an alkali metal salt of a carboxylic acid selected from the group consisting of formic acid, acetic acid, propionic acid, butyric acid, lactic acid, gluconic acid, succinic acid and citric acid.

32. A concentrate as defined in claim 22 wherein said alkylpolyglycoside surfactant has the formula $RO(R_1O)_mG_r$ where R is an alkyl group or alkenyl group having from about 8 to about 22 carbon atoms, $R_1$ is an alkyl group having 2 or 3 carbon atoms, m is a number of 0 to 10, G is a residue of a reducing saccharide and r is a number of from 1.4 to about 3.0.

33. A concentrate as defined in claim 22 wherein one of the alkylpolyglycoside surfactants is a polyglycoside having a mixed $C_8$ $C_{10}$ alkyl moiety.

34. A concentrate as defined in claim 22 wherein one of the alkylpolyglycoside surfactants is a polyglycoside having a mixed $C_{12}C_{14}C_{16}$ alkyl moiety.

35. A concentrate as defined in claim 22 wherein said anionic surfactant comprises at least one salt selected from the group of consisting of salts of alkyl sulfates, alkyl sulfonates, alkyl aryl sulfonates, alkyl ether sulfates, alpha olefin sulfonates, alkyl aryl ether sulfates, sulfated alcohols and ethoxylated sulfated alcohols, taurates, petroleum sulfonates, alkyl naphthalene sulfonates, alkyl sarcosinates and alkyl sulfosuccinates in which the alkyl group contains from about 8 to about 22 carbon atoms and the aryl group is phenyl or naphthyl.

36. A concentrate as defined in claim 35 wherein said anionic surfactant is a sodium, ammonium or magnesium salt of an alkyl sulfate or ethoxylated alkyl sulfate in which the alkyl group contains from about 8 to about 18 carbon atoms and the number of ethoxylate groups is from 1 to about 8.

37. A concentrate as defined in claim 36 wherein said anionic alkyl sulfate surfactant is sodium or ammonium lauryl sulfate and said anionic ethoxylated alkyl sulfate is sodium, ammonium or magnesium laureth sulfate or oleth sulfate.

38. A concentrate as defined in claim 22 wherein said amphoteric surfactant comprises a betaine, sultaine, aminopropionate or imidazoline derivative.

39. A stable, pumpable, flowable and pourable surfactant concentrate consisting essentially of (a) an anionic surfactant comprised of a sodium, ammonium or magnesium salt of an alkyl sulfate or ethoxylated sulfate in which the alkyl group contains from about 8 to about 22 carbon atoms;

(b) an alkylpolyglycoside surfactant having the formula $ROG_r$ where R is an alkyl group having from about 8 to about 22 carbon atoms, O is oxygen, G is the residue of a reducing saccharide and r is a number from 1.4 to about 3;

(c) a viscosity-adjusting agent selected from the group consisting of inorganic and organic electrolytes; and (d) water wherein the total surfactant (a) and (b) present in the concentrate is from about 30% to about 90% by weight, and said anionic surfactant comprises at least about 30% by weight of the total surfactant and the ratio of alkylpolyglycoside surfactant to anionic surfactant is from about 3:1 to about 1:1, and wherein the alkylpolyglycoside surfactant comprises at least two alkylpolyglycosides of two different average alkyl moieties.

40. A concentrate as defined in claim 39 wherein said inorganic electrolyte is a chloride or sulfate salt of sodium or potassium and said organic electrolyte is a sodium or potassium salt of an organic carboxylic acid selected from the group consisting of acetic acid, propionic acid, lactic acid, succinic acid and citric acid.

41. A concentrate as defined in claim 39 wherein a polyethylene glycol is added to said mixture as an additional viscosity-adjusting agent.

42. A concentrate as defined in claim 41 wherein said polyethylene glycol has a molecular weight of about 400.

* * * * *